(12) United States Patent
Ekvall et al.

(10) Patent No.: US 8,734,475 B2
(45) Date of Patent: May 27, 2014

(54) MEDICAL IMPLANT WITH FLOATING MAGNETS

(75) Inventors: Craig A. Ekvall, East Bethel, MN (US); Eric Whitbrook, St. Paul, MN (US)

(73) Assignee: Torax Medical, Inc., Shoreview, MN (US)

(*) Notice: Subject to any disclaimer, the term of this patent is extended or adjusted under 35 U.S.C. 154(b) by 0 days.

(21) Appl. No.: 13/584,303

(22) Filed: Aug. 13, 2012

(65) Prior Publication Data

US 2013/0053874 A1 Feb. 28, 2013

Related U.S. Application Data

(60) Provisional application No. 61/526,314, filed on Aug. 23, 2011.

(51) Int. Cl.
*A61B 17/08* (2006.01)
(52) U.S. Cl.
CPC ..................................... *A61B 17/08* (2013.01)
USPC .......................................................... 606/157
(58) Field of Classification Search
CPC .. A61B 17/08; A61B 17/10; A61B 17/12009; A61F 2/00; A61F 2/02; A61F 2/28
USPC .......................... 606/151, 157, 201, 213, 216; 623/23.68, 1.11–15.12, 16.11–21.19, 623/22.11–23.47, 23.64–23.71
See application file for complete search history.

(56) References Cited

U.S. PATENT DOCUMENTS

| | | | |
|---|---|---|---|
| 7,175,589 B2 | 2/2007 | Deem et al. | |
| 7,695,427 B2 | 4/2010 | Kugler et al. | |
| 2005/0209682 A1 | 9/2005 | Abraham-Fuchs et al. | |
| 2009/0204205 A1* | 8/2009 | LaRose et al. | 623/3.13 |

FOREIGN PATENT DOCUMENTS

EP 1676601 7/2006

* cited by examiner

*Primary Examiner* — Kathleen Holwerda
*Assistant Examiner* — Sarah W Aleman
(74) *Attorney, Agent, or Firm* — Ropes & Gray LLP; Jeffrey H. Ingerman

(57) ABSTRACT

Systems and methods are described for the use of floating magnetic elements in medical implants. The magnetic elements within the medical implant are allowed to rotate freely to align with a strong external magnetic field, such as that of an MRI scanner, and align to attract each other during the normal functioning of the medical implant in the absence of a strong external magnetic field.

11 Claims, 11 Drawing Sheets

MEDICAL IMPLANT WITH FLOATING MAGNETS

CROSS REFERENCE TO RELATED APPLICATION

This claims the benefit of copending, commonly-assigned U.S. Provisional Patent Application No. 61/526,314, filed Aug. 23, 2011, which is hereby incorporated by reference herein in its entirety.

BACKGROUND OF THE INVENTION

This invention relates to medical implants containing magnetic material placed around a tissue or body structure, where the medical implant can be made more compatible with competing magnetic fields, such as those present during Magnetic Resonance Imaging (MRI), by employing "floating" magnets.

Strong magnetic fields such as those within an MRI scanner can cause magnetic material in a medical implant to depolarize or repolarize, and also can induce undesirable forces on the medical implant. The magnetic field may induce a torsional force that attempts to align the magnetic poles within the implant to the magnetic field. This force can result in undesirable stress on the patient's body tissues, or on the implant itself. If the magnetic field is of sufficient strength, and the magnets in the implant cannot move to align themselves with the magnetic field, the magnetic field can cause the magnetic poles of some or all of the magnets in the implant to reorient (repolarize) to align with the magnetic field. If the poles of some magnetic elements within a medical implant reorient and some do not, resulting in poles not all in the same orientation, the unaligned poles could neutralize each other and cause a loss or reduction of magnetism (depolarization). This may result in the implant functioning poorly or not at all even after the magnetic field is removed (e.g., after the MRI scan is complete).

SUMMARY OF THE INVENTION

Systems and methods are described for the use of "floating" magnetic elements (e.g., magnets) in medical implants. As described herein, the magnetic elements within the medical implant are allowed to rotate freely to align with an external magnetic field, such as the magnetic field created by an MRI scanner. Allowing the poles of the magnetic elements to float and freely align themselves with other stronger magnetic fields such as within an MRI scanner can prevent the undesirable outcomes described above. An illustrative use of the invention is as an alternative to anti-esophageal-reflux medical devices previously described in, e.g., commonly-assigned U.S. Pat. Nos. 7,175,589 and 7,695,427. In this alternative, variants of which are shown in the drawings below, magnetic elements that float in individual housings are used in place of the fixed magnets of the previous embodiments.

The magnetic elements and/or housings can be of any shape and size so long as the magnetic elements are allowed to float or rotate within the casing. Additionally, any number of magnetic elements can be used within a single housing so long as the magnetic elements are allowed to float or align with whatever external magnetic field is strongest. Furthermore, the housings can be linked together in any suitable way, as long as the implant is sufficiently flexible to interact with body organs and/or tissue as intended. Such a flexible linkage, or the members making up the flexible linkage, can be made from polymers, metals, textiles, etc. The flexible linkage serves to allow the individual housings to move apart from each other when external forces overcome the attractive forces between magnetic elements within adjacent housings of the medical implant. In some embodiments, the flexible linkage should also serve to limit the allowable separation distance between the housings of the medical implant.

The flexible linkage may engage each of the housings in numerous ways provided that the connection between the flexible linkage and each of the housings does not impair the ability of magnetic elements within each of the housings to freely rotate. In some embodiments, the housings may be bead-shaped and may be strung together with thin flexible members such as suture or wire. Bead-shaped housings also may be linked via interwoven flexible strands, individual links, or chain links. Alternatively, bead-shaped housings may also be linked together by flexible fabric or can be encapsulated in a flexible fabric or polymeric structure (e.g., a band) to contain the bead-shaped housings. Additionally, to ensure that excessive tissue ingrowth into or about the housings and/or flexible linkages of the medical implant does not prevent the medical implant from functioning as intended, the surfaces of the housings and/or the flexible linkages may be coated with one or more polymers, drugs, or biologics to modulate tissue growth.

In each of these embodiments, in the absence of a strong external magnetic field, the magnetic fields of the magnetic elements within the medical implant will predominate, attracting the housings to one another to perform the desired medical function. In some embodiments, in the presence of a strong external magnetic field, such as that of an MRI scanner, the magnetic elements may rotate within the housings to align with the stronger field. While the magnetic elements may, therefore, not perform the desired medical function during that time, the flexible member will prevent the implant from completely failing, and the implant will be able to resume its function once the strong external magnetic field is removed.

BRIEF DESCRIPTION OF THE DRAWINGS

Further features of the invention, its nature and various advantages will be apparent upon consideration of the following detailed description, taken in conjunction with the accompanying drawings, in which like reference numbers refer to like parts throughout, and in which.

DETAILED DESCRIPTION

Figure 1:
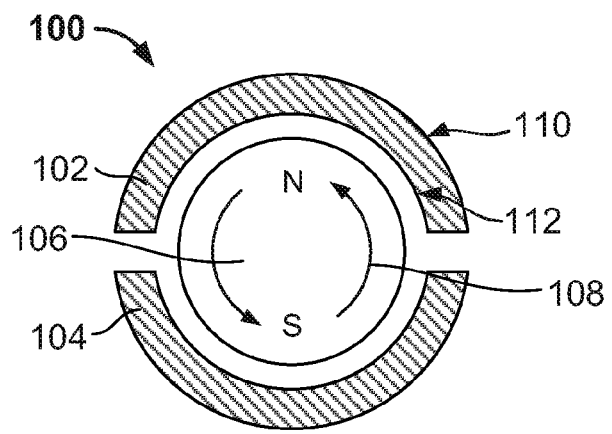
FIG. 1 depicts a housing which is made from a spherical magnetic element encased in two spherical shell halves.

Systems and methods are described for the use of "floating" magnetic elements in medical implants. The medical implant includes a series of housings, which encapsulate the magnetic elements. Each housing allows its respective magnetic element or elements to rotate freely in order to align with the magnetic fields of magnetic elements in adjacent housings of the medical implant or magnetic fields external to the medical implant. The housings are connected by a flexible linkage, which engages each of the housings, but which does not impair the rotation of the magnetic elements within the housings. The flexible linkage may also accommodate the various circumferential sizes associated with the medical implant.

The medical implant may include a pressure-mediated device placed around a patient's tissue structure, body organ, or body lumen to control the rate of fluid, solid, or other content passage through the tissue structure. The tissue structure may be, for example, the esophagus, stomach, duodenum, rectum, urethra, or other tissue structure. The medical implant is movable between at least two states in response to the pressure within the tissue structure. The medical implant may control more than one rate of passage through the tissue structure. The medical implant is preferably self-regulating between the flow rates in response to the pressure within the tissue structure.

For example, in response to pressure within the tissue structure, such as food passing through the lumen about which the medical implant is placed, the circumference of the medical implant may expand. During an expanded state, the constricting force applied to the tissue structure caused by the magnetic attraction between the magnetic elements of the medical implant may be reduced due to the increased distance between the magnetic elements. The reduction in force applied to the tissue structure may allow the food to pass unencumbered. In contrast, when the pressure within the tissue structure is reduced (e.g., when food is not passing through the lumen), the medical implant may be unexpanded. During an unexpanded state, the distance between magnetic elements is reduced, increasing the magnetic attraction between the magnetic elements as well as the force applied to the tissue structure. The constriction of the tissue structure may aid in the prevention of unwanted material (e.g., stomach acid) from traversing the lumen.

In some embodiments, medical implants as described herein may be used for the treatment of gastroesophageal reflux disease as discussed in commonly-assigned U.S. Pat. No. 7,695,427, which is hereby incorporated by reference herein in its entirety. In some embodiments, medical implants as described herein may also be used in gastric banding as discussed in greater detail in, for example, commonly-assigned U.S. Patent Publication No. 2009/0062824, which is hereby incorporated by reference herein in its entirety.

Furthermore, in accordance with embodiments of the invention, the magnetic elements within the medical implant are allowed to rotate freely to align with an external magnetic field, such as that of an MRI scanner. Allowing the poles of the magnetic elements to float and freely align themselves with other stronger magnetic fields (e.g., within an MRI scanner) may prevent the loss of functionality of the medical implant as discussed above. In such cases, after removal of the stronger magnetic fields (e.g., outside an MRI scanner), the magnetic elements may rotate and align themselves with each other and resume their medical functionality.

In the medical implant, a magnetic element may be encapsulated within a housing. As used herein, a magnetic element may be any structure, composition or device that produces or affects, even temporarily, a magnetic field. For example, in some embodiments, a magnetic element may include permanent magnets, temporary magnets, electromagnets, or a combination thereof (e.g., a ferromagnetic material that is magnetically attracted to a permanent magnet). Magnetic elements may include any material (e.g., samarium, neodymium, etc.), shape (e.g., rings, disks, spheres, bars, etc.), or size applicable for use in a medical implant. In some embodiments, the strength of the magnetic elements found throughout a single medical implant may be consistent. In some embodiments, the strength of the magnetic elements found throughout a single medical implant may vary. In some embodiments, the strength of the magnetic elements, whether consistent or varied, may be keyed towards a specific medical function. For example, the resistance to opening the medical implant from one state to the next may vary based on the particular body tissue around which the medical implant is intended to be situated.

The composition and mass of adjacent magnetic elements and the space between each magnetic element determine a specific amount of force that is required to separate the magnetic elements (e.g., by overcoming the magnetic attraction between the magnetic elements) when the medical implant is in a closed state. At the same time, the maximum separation that should be allowed between the magnetic elements when the medical implant is in an opened state should not be so great that the magnetic attraction between the magnetic elements at that separation distance is insufficient to restore the medical implant to a closed state. In some embodiments, the medical implant may be structured to limit the maximum distance the magnetic elements may be separated from each other based on the strength of the magnetic elements and/or the resistance, if any, that the body organ or tissue structure may produce during the normal functioning of the organ or tissue structure. The distance that circumferentially adjacent magnetic elements may move apart from each other as well as the amount of circumferential geometry that must be maintained by the medical implant during an opened state may be determined based on the particular medical function.

Figure 7A:
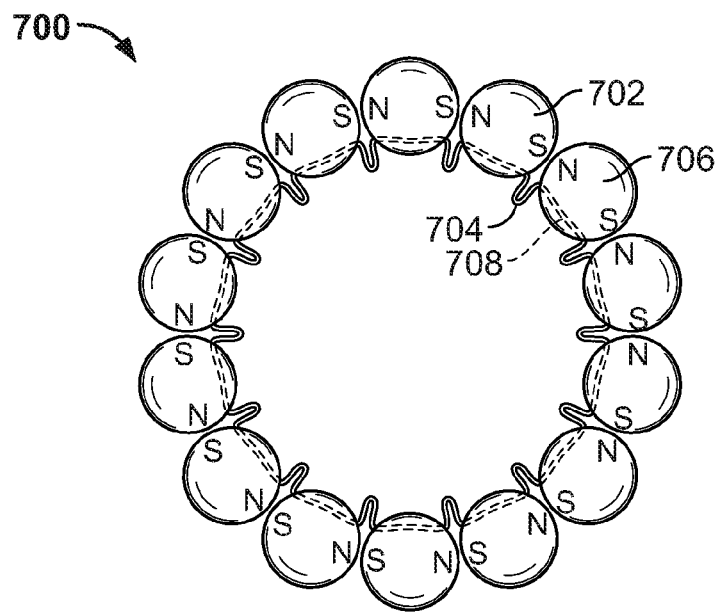
FIG. 7A shows how the magnetic elements in each of the housings of the medical implant align and attract each other to form a closed state with all the housings touching.
Figure 7B:
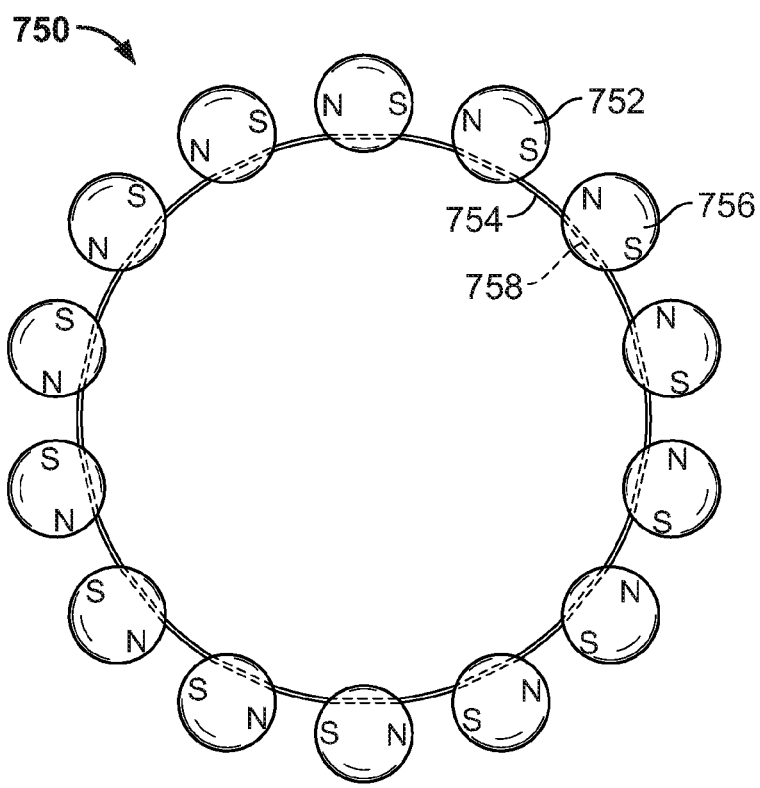
FIG. 7B shows how when sufficient forces exist to separate the housings, the housings move away from each other to an alternative opened state.

Each magnetic element may be magnetized, at least temporarily, such that it has one magnetic pole (e.g., North or "N" as shown below in FIGS. 1, 3-5, and 7A-B) and an opposite magnetic pole (e.g., South or "S" as shown below in FIGS. 1, 3-5, and 7A-B). Each magnetic pole of each magnetic element is attracted to the opposite magnetic pole of the remaining magnetic elements in the medical device. When arranged in series in the medical implant (e.g., as shown in FIGS. 7A-7B), the magnetic pole of each magnetic element will align to attract the opposite magnetic pole of an adjacent magnetic element.

In embodiments of this invention, the magnetic element may "float" or rotate within a housing. As used herein, a housing refers to any material, which, partially or completely, covers or contains a magnetic element. For example, in some embodiments, a housing may include a spherical bead which encapsulates the magnetic element. The housing may include any material (e.g., metals, polymers, textiles, etc.), shape (e.g., sphere, egg, cube, etc.), or size applicable for use in a medical implant. In some embodiments, the housing may include a coating or other applicable feature to facilitate implantation into a patient or to limit excessive tissue growth into or about the medical implant once it has been implanted as excessive tissue growth may prevent the medical implant from functioning as intended. The coating may include additional polymers, drugs, and/or biologics, to modulate tissue ingrowth after implantation. In some embodiments, multiple magnetic elements may be located within the same housing.

In some embodiments, the magnetic elements may rotate sufficiently to align their poles with the magnetic fields of other magnetic elements or other stronger magnetic fields such as within an MRI scanner. For example, in the absence of a strong external magnetic field, the magnetic elements found within each of the housings of the medical implant may attract each other to circumferentially compress the body tissue by applying a vector force towards the center point of the medical implant or body tissue around which the medical implant is positioned. In some embodiments, the medical implant may reach a closed state (e.g., a circumference of the medical device defined by contact between the housings), in which despite the attraction of the magnetic fields, the circumference of the medical implant no longer decreases. While the magnetic elements attract each other, the medical implant may compress the body tissue to produce a desirable medical effect. In some embodiments, a desirable medical effect may be achieved even if the medical implant does not achieve a fully closed state.

Upon the application of a strong external magnetic field, due to the ability of the magnetic elements to rotate, the magnetic elements may align themselves with the strong external magnetic field. Under the influence of the strong external magnetic field, the magnetic fields may not circumferentially compress the body tissue. This may allow the body tissue to expand in a radially outward direction in the absence of a constricting force applied by the medical device. While in such a situation, the magnetic elements may not be performing the desired medical function, the temporary lack of performance may be preferable to changes in the medical implant (e.g., the partial or complete depolarization of the magnetic elements), which may result in the medical implant functioning poorly or not at all after the strong external magnetic field is removed. Moreover, the linkage binding the magnetic elements together may prevent the medical implant from partially or completely failing to function, even while the strong external magnetic field is in place. For example, the medical implant may reach an opened state (e.g., a circumference of the medical device defined by the inelasticity of the member), in which despite radially outward forces exerted on the medical implant, the circumference of the medical implant no longer increases. In some embodiments, if the strong external magnetic field is removed, the magnetic elements within the medical implant may re-align, and the medical implant may return to a closed state and then resume its medical function. As the magnetic elements align, the magnetic attraction between the magnetic elements may generate a force or pressure which resumes constricting or compressing the body tissue.

In some embodiments, the magnetic elements may re-align with each other in a step-wise fashion about the medical implant. For example, the re-alignment of an initial magnetic element within the medical implant may influence magnetic elements adjacent to the initial magnetic element to re-align as well. As each magnetic element re-aligns, additional magnetic elements may be influenced until all magnetic elements are aligned.

In some embodiments, the housings may include additional surface features such as grooves, channels, through holes, adhesives, coarse areas, hooks, loops, or other fasteners used by the housing to receive a flexible member. In some embodiments, the surface features may partially or completely bisect the surface area of the housing. In some embodiments, the surface features may, partially or completely, bore, indent, or pass through the housing. The surface features may be any length about the surface area of the housing or through the housing. The surface features may also run from any one point on the surface area of the housing to any other point on the surface area of the housing. In some embodiments, the surface features may run continuously or intermittently from one point to another point on the surface area of the housing.

In some embodiments, one housing may be attached to another housing through a member. As used herein, a member may be any linkage (e.g., a structure, composition, or device) or portion of a linkage that connects or links multiple housings together that is sufficiently flexible to allow the implant to interact with body tissues as intended. For example, in some embodiments, a member may include threaded flexible strands, criss-crossing or interwoven flexible strands, independent or chain links of various sizes, or a flexible fabric- or polymer-based band or bands, each of which may be received by a surface feature of the housing.

In some embodiments, the housings may be bead-shaped and may be strung together with thin flexible strands such as suture or wire. The flexible strands may reside in, pass through, or otherwise be received by surface features found on the surface area of each of the housings. In some embodiments, housings may be linked via independent links or chain links, of varying sizes, and the links may reside in, pass through, or otherwise be received by surface features found on the surface area of each of the housings. In some embodiments, the housings may be linked together by a flexible band, which includes a flexible fabric or polymeric structure. In some embodiments, a portion of the flexible band may reside in, pass through, or otherwise be received by surface features of each housing. In some embodiments, the flexible band may bind each of the housings by partially or completely covering the housing.

In some embodiments, when a member and a surface feature of a housing contact, a projection of the member may enter the recess of the surface feature. The insertion of the projection into the surface feature may act to mechanically prevent the member from leaving or moving away from the surface feature and, therefore, bind the housing to the member. The member may engage the housing in any one or more of numerous ways (e.g., passing through, boring into, or attaching to the housing or to a surface feature). Furthermore, in some embodiments, the member may penetrate the interior volume of the housing containing the magnetic element(s), as long as it does so in a way that does not impair the ability of the magnetic element(s) to freely rotate. In some embodiments, a plurality of housings may be bound to one or more members. In addition, in some embodiments, the magnetic attraction, or lack thereof, of the magnetic elements may vary the amount of tension experienced by the member. For example, when magnetically attracting each other, the circumferentially adjacent magnetic elements may reduce the diameter of the medical implant to a closed state. In such cases the body tissue around which the medical implant is located may be squeezed or have a reduced diameter. During this closed state the tension experienced by the member may be reduced. In contrast, when the circumferentially adjacent magnetic elements are not magnetically attracting each other (e.g., because of the presence of a strong external magnetic field), the body tissue around which the medical implant is located may expand, increasing the diameter of the medical implant to an opened state. In an opened state, the tension applied to the member may increase, relative to the tension applied to the member during a closed state.

In some embodiments, the member may elastically expand or deform (e.g., bend) as the circumference of the medical device is expanded. As the member elastically expands or deforms, tension in the member may mechanically prevent further expansion of the body tissue and medical implant. In some embodiments, structural features of the member may act in lieu of, or in combination with, elastic expansion as the circumference of the medical device is expanded. The ability of the medical device to expand and contract from one state to another may depend on structural features of the member (e.g., folds, creases, links, etc.), which allow the medical implant to vary its circumferential size without varying the overall length of the member. For example, a member may fold (or unfold), or the links making up a member may reposition themselves to maximize (or minimize) the distance between adjacent housings. When the circumferential size of the medical implant and the length of the member are equal (e.g., the member is completely unfolded), tension in the member may mechanically prevent further expansion of the body tissue and medical implant. Furthermore, in some embodiments, the housings may slide or translate along the length of the member allowing the distance between individual housings of the medical implant to vary.

In some embodiments, the member may also include a clasp connecting one end of the member to the other end of the member. A clasp may include any structure, device, or adhesive used to bind the ends of a member, or multiple members, together. In some embodiments, a clasp may be activated once the medical implant is positioned around a body tissue. Clasps for medical implants are discussed in greater detail in, for example, commonly-assigned U.S. Patent Publication No. 2011/0098731, which is hereby incorporated by reference herein in its entirety.

The member may include any material (e.g., polymers, metals, textiles, etc.), including, but not limited to, shape-memory or biocompatible alloys or polymers. In addition, in some embodiments, the member may include a coating or other applicable feature as discussed above, to modulate tissue ingrowth after implantation. The member may be any size or shape which allows the medical implant to perform its function, including, but not limited to, allowing the medical implant to vary its circumference about a body tissue in response to various forces being exerted onto the medical implant. In some embodiments, the member may act as a limit on the allowable separation distance. For example, a member for a particular medical implant may be selected based on the size or orientation of the body tissue which it may surround. The member may be appropriately sized to ensure that during an opened state the medical implant does not translate along the body tissue. In some embodiments, the member may be of an elastic material. The member may elastically lengthen in the circumferential direction in response to a decrease in the magnetic attraction between the magnetic elements as the body tissue applies a force to enlarge the circumference of the medical implant. In response to a magnetic attraction between the magnetic elements, which overcomes the force applied by the body tissue, the medical implant may decrease its circumference. The member may also decrease its circumference elastically, or via structural features, as the medical implant obtains a closed state.

FIG. 1 depicts an embodiment of a housing which is made from a spherical magnetic element encased in two spherical shell halves. FIG. 1 shows housing 100, which includes a first spherical half 102 and a second spherical half 104 encapsulating magnetic element 106. First spherical half 102 and a second spherical half 104 may be attached to each other through any suitable means (e.g., welding, adhesives, snap-fit, tongue-and-groove, etc.) to house magnetic element 106. In addition, in some embodiments, the housings (e.g., housing 100) of the medical implant may be formed from a single structure (e.g., not formed from the combination of two halves), or may be formed from any number of component structures (e.g., formed from thirds, quarters, etc.). First spherical half 102 and a second spherical half 104 may be configured to allow the magnetic element to rotate freely as indicated by arrow 108. In addition, first spherical half 102 and a second spherical half 104 may include a structure with outside surface 110 and inside surface 112. In some embodiments, outside surface 110 may define the surface of housing 100, and inside surface 112 may define the volume of housing 100 in which magnetic element 106 may freely rotate.

Figure 2:
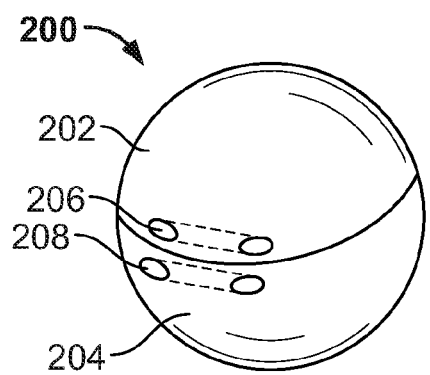
FIG. 2 depicts a housing such as that in FIG. 1, which contains through holes which accept a flexible linkage, or a member of a flexible linkage, to allow the housing to be interconnected with other housings.

FIG. 2 depicts a housing such as that in FIG. 1, which contains through holes which accept a flexible member to allow the housings to be interconnected. FIG. 2 shows housing 200, which includes a first spherical half 202 and a second spherical half 204. In addition, housing 200 includes a through hole 206, a continuous passageway through the housing formed from an opening at one point on the surface of housing 200 to an opening at a second point on the surface of housing 200. In some embodiments, through hole 206 may pass completely through the housing. For example, through hole 206 may originate at the outside surface (e.g., outside surface 110 (FIG. 1)) of housing 200 and terminate within (e.g., at inside surface 112 (FIG. 1)) housing 200. In some embodiments, through hole 206 may pass within the structure of housing 200. For example, through hole 206 may originate at one point on the surface (e.g., outside surface 110 (FIG. 1)) of housing 200 and terminate at another point on the surface (e.g., outside surface 110 (FIG. 1)) of housing 200 without breaching housing 200 (i.e., reaching inside surface 112 (FIG. 1)).

In some embodiments, housing 200 may have multiple surface features, including, but not limited to, multiple through holes (e.g., through hole 206 and through hole 208). Each through hole may be configured to receive a member. In some embodiments, a member may traverse through hole 206, and a different member may traverse through hole 208. In some embodiments, through holes on particular housings may align with through holes on adjacent housings to receive a common member, which is threaded through the through holes on adjacent housings.

Figure 3:
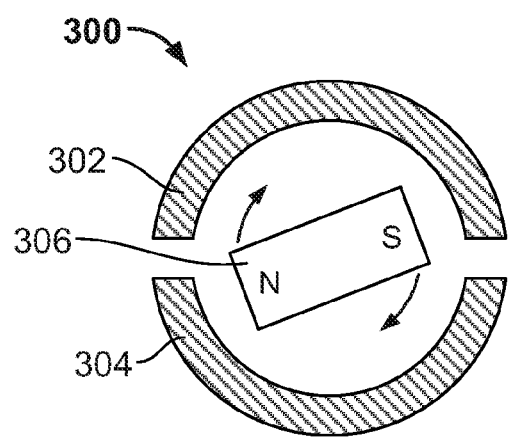
FIG. 3 shows a rectangular magnetic element encased in a spherical housing, in which the magnetic element may rotate freely.

FIG. 3 shows a rectangular magnetic element encased in a spherical housing, in which the magnetic element may rotate freely. FIG. 3 shows housing 300, which includes a first spherical half 302 and a second spherical half 304. Housing 300 contains magnetic element 306. Magnetic element 306 is a non-spherical magnetic element. In some embodiments, a magnetic element may include a ring, cube, egg, or any other irregular shape as long as its shape does not prevent it from rotating. In addition, in some embodiments, the inside surface (e.g., inside surface 112 (FIG. 1)) of housing 300 may include a non-spherical shape as long as its shape does not prevent magnetic element 306 from rotating.

Figure 4:
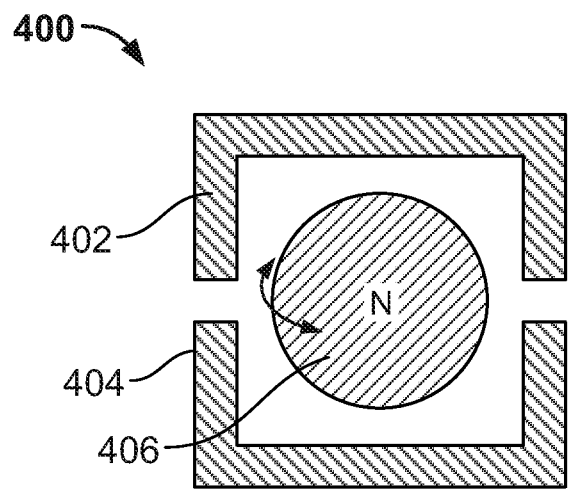
FIG. 4 shows a cylindrical or disk-shaped magnetic element encased in a rectangular housing, in which the magnetic element may rotate freely.
Figure 5:
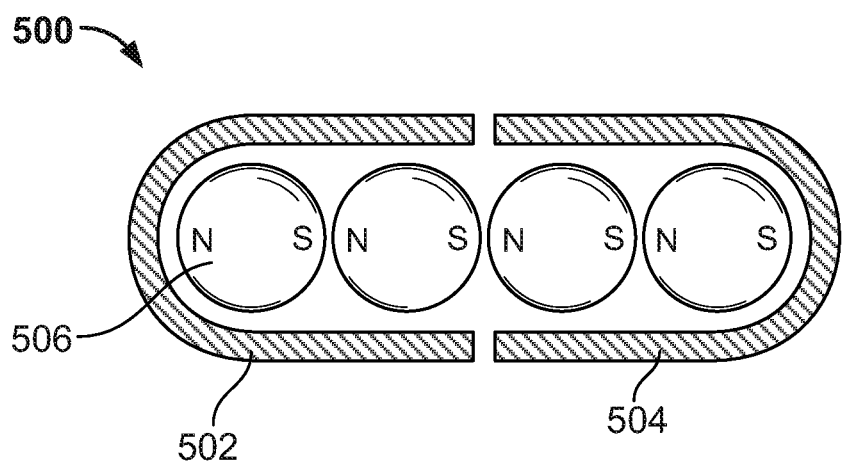
FIG. 5 shows a plurality of magnetic elements housed within a single capsule-shaped housing, in which the magnetic elements may rotate freely.

For example, FIGS. 4 and 5 show some embodiments, in which the inside surface (e.g., inside surface 112 (FIG. 1)) of housing 300 is non-spherical. FIG. 4 shows a cylinder or disk-shaped magnetic element 406 housed in a rectangular housing 400. Housing 400 includes a first rectangular half 402 and a second rectangular half 404. Within the enclosure formed by rectangular half 402 and a second rectangular half 404, cylindrical or disk-shaped magnetic element 406 may rotate freely. In some embodiments, the size of the area formed within housing 400 by the combination of first rectangular half 402 and a second rectangular half 404 may be affected by the size and thickness of first rectangular half 402 and second rectangular half 404. Therefore, in some embodiments, the size, shape, and orientation of a magnetic element (e.g., magnetic element 406) may depend on the size, shape, and orientation of the associated housing (e.g., housing 400). Likewise, in some embodiments, the size, shape, and orientation of a housing (e.g., housing 400) may depend on the size, shape, and orientation of the associated magnetic element (e.g., magnetic element 406).

FIG. 5 shows a plurality of magnetic elements housed within a single capsule-shaped housing, in which the magnetic elements may rotate freely. FIG. 5 shows housing 500, which includes a first non-spherical half 502 and a second non-spherical half 504. Within the enclosure formed by first non-spherical half 502 and second non-spherical half 504, a plurality of magnetic elements, including magnetic element 506, may rotate freely. In some embodiments, the plurality of magnetic elements may be separated by additional structures. For example, in some embodiments, multiple housings, each including one or more magnetic elements, may be encapsulated within another, larger housing.

Figure 6:
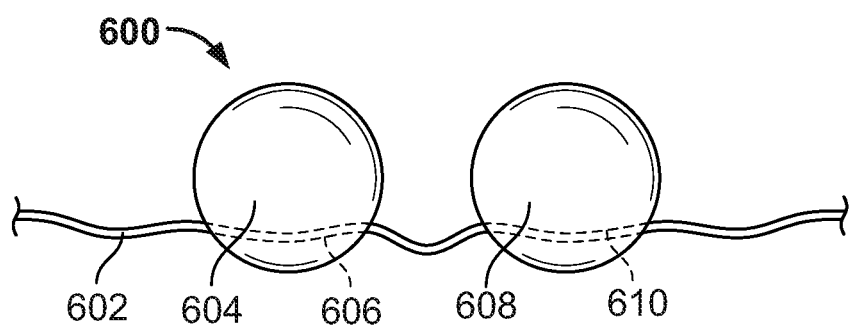
FIG. 6 shows how two housings may be connected by a flexible member traversing through holes located in each of the housings.

FIG. 6 shows how two housings may be connected by a flexible member traversing through holes located on each of the housings. FIG. 6 shows medical implant 600, which includes housing 604 and housing 608 connected by member 602. In this embodiment, member 602 is a flexible strand that is received by through hole 606 of housing 604 and through hole 610 of housing 608. Multiple housings may be connected together by a single member although only two are shown in FIG. 6 for simplicity. Each of housing 604 and housing 608 may contain one or more magnetic elements (e.g., magnetic element 106 (FIG. 1)).

In medical implant 600, member 602 is threaded into through holes in adjacent housings. In some embodiments, multiple members may be threaded through one or more through holes on adjacent housings. In addition, in some embodiments, a housing may have multiple through holes (e.g., as shown above in FIG. 2). One or more members may be threaded through one or more of the through holes on each of the housings. In some embodiments, a medical implant may include multiple members, in which each member is not threaded through every one of the housings in the medical implant.

FIG. 7A shows how the magnetic elements in each of the housings of the medical implant align and attract each other to form a closed state with all the housings touching. FIG. 7A shows medical implant 700. Medical implant includes a plurality of housings (e.g., housing 702 and housing 706) connected by member 704. In this embodiment, member 704 is a flexible strand that is received by a through hole (e.g., through hole 708) located in each of the plurality of housings of medical implant 700. When the magnetic elements are not affected by external forces, the magnetic elements align with, and attract, each other. For example, as shown by FIG. 7A, the poles of each magnetic element align with the opposite pole on an adjacent magnetic element (e.g., the north pole of a magnetic element aligns with the south pole of an adjacent magnetic element) as discussed above.

While the magnetic elements attract, tension on the member is reduced. For example, in some embodiments, adjacent magnetic elements may attract each other until the housings associated with the magnetic element are in contact. The member may include structural features such as folds or crimps to adjust the circumferential length of the medical implant. In some embodiments, the member may elastically expand or contract based on the circumference of the medical implant. In this closed state, the medical implant may be suitable for its medical function.

FIG. 7B shows how, when sufficient forces exist to separate the housings, the housings move away from each other to an alternative open state. In the opened state, the distance between each of the housings is limited by the flexible member or members connecting each of the housings. For example, medical implant 750 may have been acted upon by an external force, which has reduced or overcome the attractive force of the magnetic elements of medical implant 750. The attraction between the magnetic elements is no longer sufficient to maintain contact between adjacent housings. In some embodiments, this may be the result of a strong external magnetic field (e.g., by the magnetic elements aligning with an external magnetic force instead of each other), or may be the result of the radially outward force of the body tissue being greater than the radially inward force of the medical implant.

Figure 8:
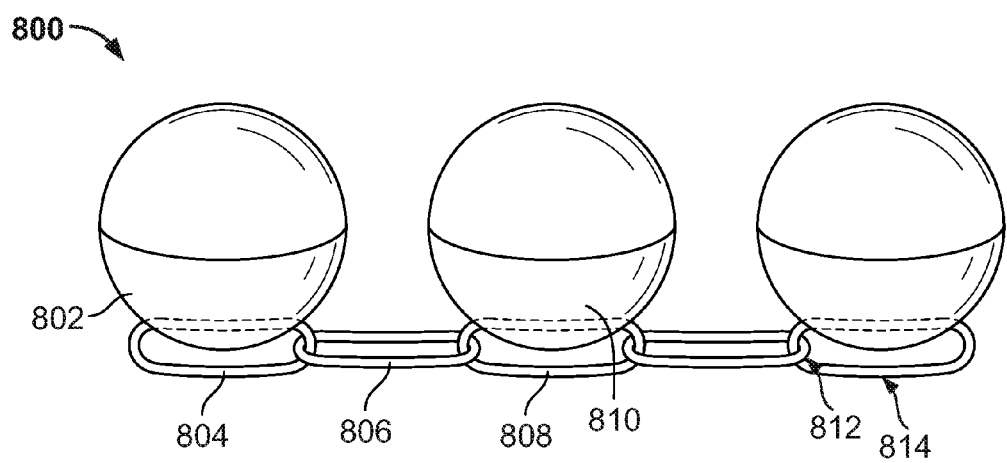
FIG. 8 shows housings that are connected by a flexible chain-type member, which allows the medical implant to achieve both opened and closed states.

FIG. 8 shows housings that are connected by a flexible chain-type member, which allows the medical implant to obtain both an opened and closed state. FIG. 8 shows medical implant 800, which includes housing 802 and housing 810. Housing 802 and 810 are connected by a member composed of several chain links (e.g., chain links 804, 806, and 808). A portion of chain link 804 traverses housing 802 via a through hole (e.g., through hole 206 (FIG. 2)) connecting chain link 804 to housing 802. Chain link 804 is linked to chain link 806, and chain link 806 is linked to chain link 808. A portion of chain link 808 traverses housing 810 via a through hole (e.g., through hole 206 (FIG. 2)) connecting chain link 808 to housing 810. In some embodiments, housing 802 and housing 810 may be able to laterally translate on chain link 804 and chain link 808, respectively, to assist in the circumferential expansion or contraction of medial implant 800.

In some embodiments, each chain link may be able to elastically deform (e.g., bend) to accommodate both an opened state and a closed state of the medical implant. In some embodiments, individual chain links may vary their position relative to other chain links, while still being linked, to accommodate both an opened state and a closed state of the medical implant. For example, the chain links included in the member may vary from a position where each link contacts an adjacent link at the widest point of each link (e.g., point 812) to a position where links contact each other at a narrower point (e.g., point 814). In some embodiments, the ability for interwoven chain links to move relative to each other may allow the medical implant to achieve an opened state in which adjacent housings do not contact each other, and a closed state where adjacent housings contact each other.

Figure 9A:
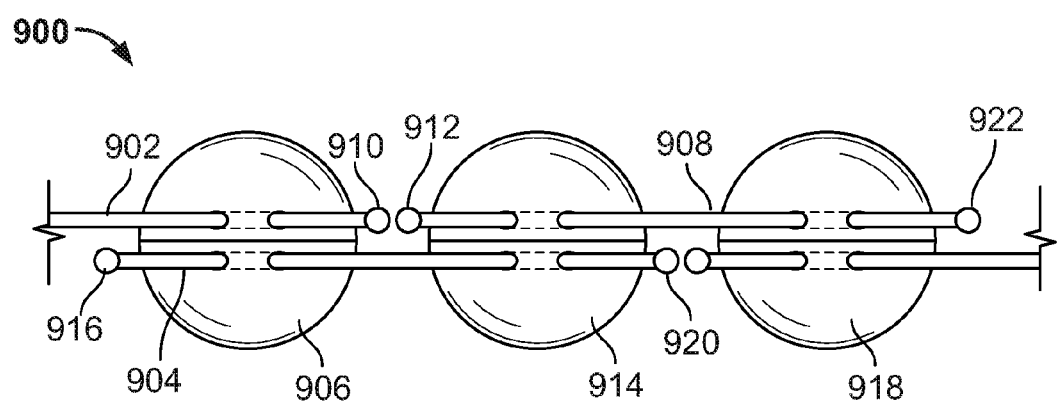
FIG. 9A shows housings that are connected by a series of independent links, which allows the medical implant to obtain both an opened and closed state.

FIG. 9A shows housings that are connected by a series of independent links, which allow the medical implant to obtain both an opened and closed state. Each independent link includes a shaft border by two enlarged ends or bearings. As used herein, a "bearing" is a portion of the independent link which cannot traverse a through hole. In some embodiments, a bearing may not be able to traverse a through hole due to its physical size. For example, the bearing may have a larger diameter than the remainder of the independent link. In some embodiments, other suitable methods (e.g., an irregularity in the shape of the bearing) that prevent a bearing from entering a through hole may be used.

The shaft of each independent link slides through two adjacent housings. The lateral motion of the independent links relative to each of the housings, or, conversely, the lateral motion of each of the housings relative to each independent link is limited by the bearings. While the shaft of the independent link is able to flow freely through the surface features of each of the housings, the bearings of the independent links may not. The length of the shaft of each independent link is great enough to allow each of the housings to move apart to an opened state, in which housings may not contact each other, but also move to a closed state where one or more of the housings are in contact.

Furthermore, each of the housings may have a second independent link sliding through a second surface feature. The second independent link connects each of the housings to another adjacent housing on the opposite side of the housing connected by the initial independent link. In an opened state, each of the housings may be in contact with a bearing on one side of one of the independent links, while also in contact with the bearing on the opposite side of the other independent link. In such embodiments, one bearing of one independent link may not be able to enter one side of a first surface feature on the housing, while a second bearing on a second independent link may not be able to enter the opposite side of a second surface feature located on the housing.

FIG. 9A shows medical implant 900, which includes housing 906, housing 914 and housing 918. Housing 906 and 914 are connected by a member, which included a series of independent links (e.g., independent links 902, 904, and 908). A portion of independent link 902 (e.g., a shaft) traverses housing 906 via a through hole (e.g., through hole 206 (FIG. 2)). In some embodiments, housing 906 may translate across independent link 902 as independent link 902 slides through a though hole in housing 906. Independent link 904 includes bearing 916, which may not pass through the through hole on housing 906.

Independent link 902 traverses housing 906 via a through hole (e.g., through hole 206 (FIG. 2)) connecting housing 906 to another housing (not shown). Housing 906 may translate on independent link 902 until it is inhibited by bearing 910. Independent link 904 traverses housing 906 via a through hole (e.g., through hole 206 (FIG. 2)) located on housing 906, and traverses housing 914 via another through hole located on housing 914. Housing 906 and housing 914 may translate freely about the length of independent link 904 between the bearings located on the ends of independent link 904. In some embodiments, during a closed state, housing 906 and housing 914 may contact each other as both housings translate along independent link 904.

Independent link 908 traverses housing 914 via a through hole (e.g., through hole 206 (FIG. 2)) located on housing 914, and traverses housing 918 via another through hole located on housing 918. Housing 914 and housing 918 may translate freely about the length of independent link 908 between the bearing 912 and bearing 922, which are located on either end of independent link 908. Through the connections of independent link 904 (e.g., connecting housing 906 to housing 914) and the connections of independent link 908 (e.g., connecting housing 914 to housing 918), the housings which make up the medical implant are held together. In addition, the ability of each of the housings to translate on its respective independent link allows the medical implant to expand and contract its circumference. For example, during a closed state, housing 918 and housing 914 may contact each other as both housings translate along independent link 908 as housing 906 and housing 914 contact each other while translating along independent link 904.

The length of each independent link and the location of each bearing may determine the amount of circumferential expansion medical implant 900 may undergo. For example, housing 906 may translate in one direction (e.g., to the left) on independent link 902, and housing 906 may translate in the opposite direction (e.g., to the right) on independent link 904. The translation of housing 906 may be stopped by the bearing associated with each independent link (e.g., bearing 910 in the case of independent link 902 and bearing 916 in the case of independent link 904) contacting the through holes (e.g., through hole 206 (FIG. 2)) of housing 906. As the bearings are unable to pass through the through hole, housing 906 may no longer be able to translate in either direction. As adjacent housings are likewise prevented from translating due to contact with bearings on other independent links the circumferential expansion of the medical implant may be limited by the length of each independent link.

For example, housings 906, 914, and 918 may translate independently of each other to provide the medical function of the medical implant. In some embodiments, the maximum circumference of the medical implant may be achieved when the bearings associated with each independent link (e.g., bearing 916 and bearing 920 for independent link 904) contact through holes on adjacent housings (e.g., housing 906 and housing 914, respectively). For example, as medical implant expands, housing 906 may translate on independent link 904 until bearing 916 contacts a through hole on housing 906. Housing 914 may likewise translate until bearing 920 contacts a through hole on housing 914. The remaining housings of the medical implant may also continue to translate on associated independent links until the bearings on each independent link contact a through hole on each of the housings. The circumference of the medical implant will then be associated with the sum of the length of each independent link.

Figure 9B:
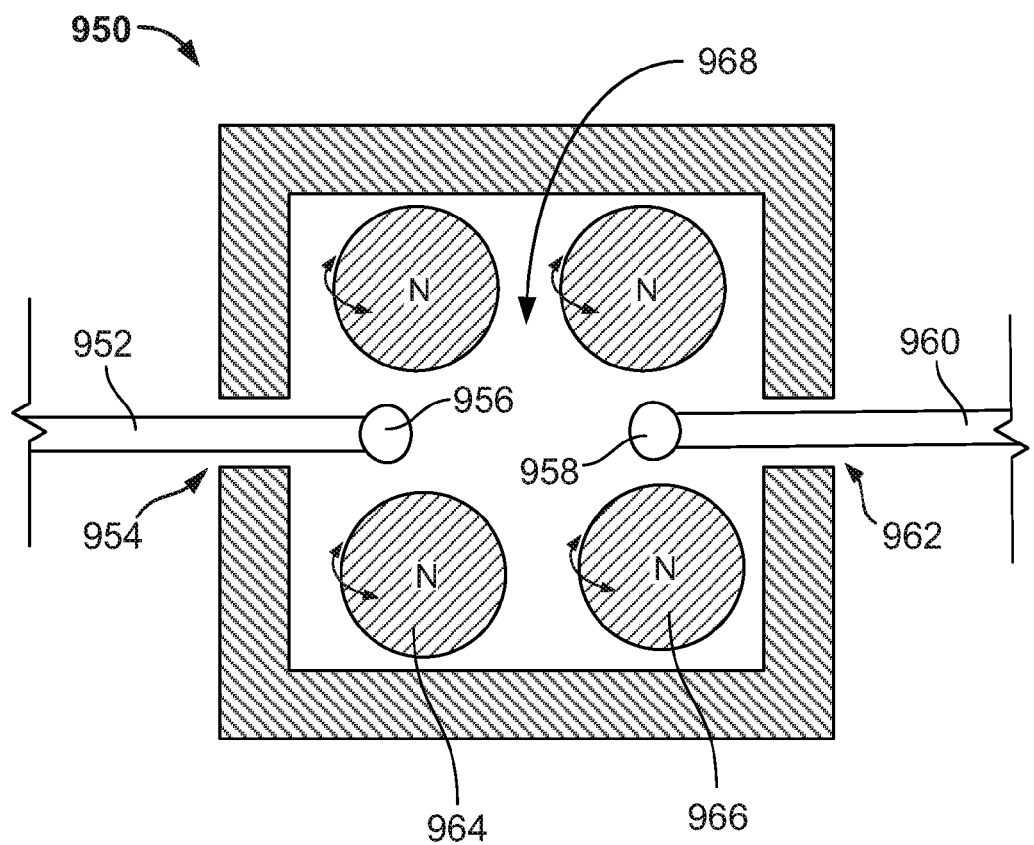
FIG. 9B shows a housing wherein the bearings of multiple independent links are located within the housing.

FIG. 9B shows a housing wherein the bearings of multiple independent links are located within the housing. In FIG. 9B, housing 950 includes independent link 952 and independent link 960, each of which may have a shaft that may traverse through hole 954 and through hole 962, respectively. Independent link 952 includes bearing 956, which is unable to traverse through hole 954. Independent link 960 includes bearing 958, which is unable to traverse through hole 962. In some embodiments, independent link 952 and independent link 960 may engage other housings (not shown) in addition to housing 950. For example, independent link 952 may include another bearing on the end of independent link 952 that is opposite bearing 956. The other bearing may be located within the other housing, which is adjacent to housing 950. The other housing may include a through hole, which the shaft of independent link 952 may traverse, but which the other bearing may not traverse. FIG. 9B also includes magnetic element 964 and magnetic element 966, which may rotate freely within housing 950, irrespective of the positions of independent link 952 and independent link 960. In some embodiments, as shown, independent link 952 and independent link 960 may penetrate interior volume 968 of housing 950, as long as it does so in a way that does not impair the ability of magnetic element 964 and magnetic element 966 to freely rotate within housing 950.

Figure 10:
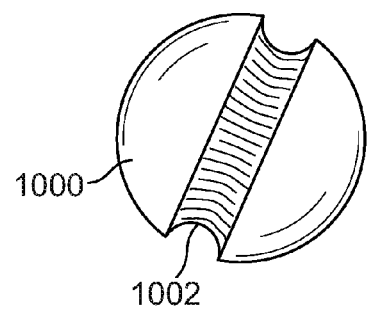
FIG. 10 shows a housing having a surface feature that can be used to link housings together as shown in FIGS. 11-13.
Figure 11:
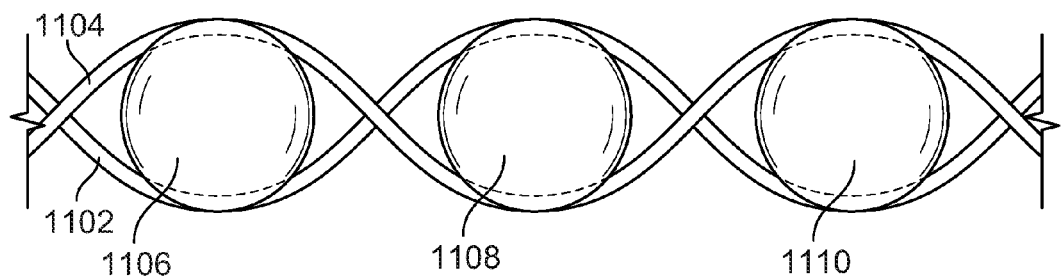
FIG. 11 shows how a flexible member can criss-cross around the housings and engage the surface features to hold the housings together.
Figure 12:
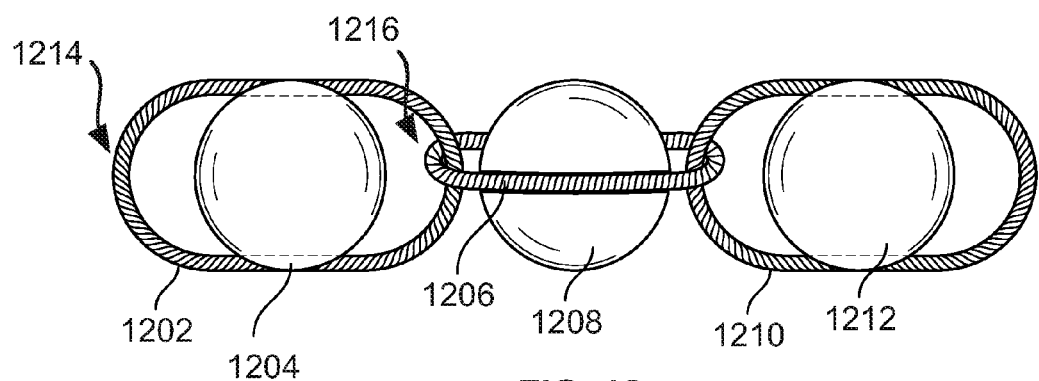
FIG. 12 shows how a flexible member can be configured as larger chain-type links that engage surface features of each of the housings.
Figure 13:
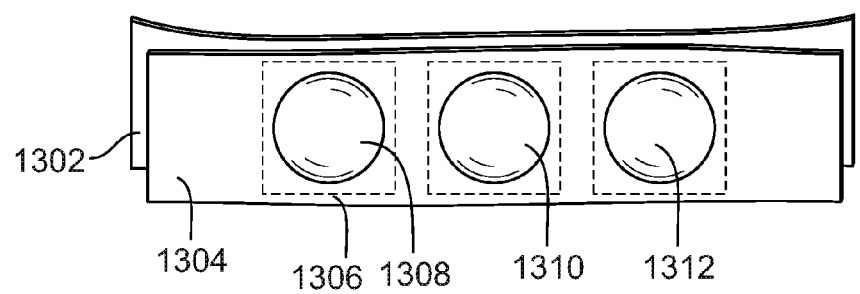
FIG. 13 shows housings that are sewn or otherwise held in pockets of one or more fabric or polymer-based flexible bands.

FIG. 10 shows a housing having a surface feature that can be used to link housings together as shown in FIGS. 11-13. In FIG. 10, housing 1000 includes surface feature 1002. Surface feature 1002 is a groove that is configured to receive a member (e.g., flexible strand 1104 (FIG. 11)). Surface feature 1002 bisects housing 1000. In some embodiments, surface feature 1002 may be any length about the surface area of the housing 1000 or may run from any one point on the surface area of the housing 1000 to any other point on the surface area of the housing 1000. In some embodiments, surface feature 1002 may run continuously or sporadically from one point to another point on the surface area of the housing 1000. In some embodiments, the groove may include varying depths or additional fastening mechanisms (e.g., adhesives).

FIG. 11 shows how a flexible member can criss-cross around the housings and engage the surface features to hold the housings together. FIG. 11 shows housing 1006, housing 1108, and housing 1110 held together by criss-crossing or interwoven members, such as flexible strand 1102 and flexible strand 1104. Flexible strand 1102 and flexible strand 1104 are received by a surface feature (e.g., surface feature 1002 (FIG. 10) as indicated by the dotted lines shown on housing 1106, housing 1108, and housing 1110. Additional embodiments incorporating flexible strands (e.g., flexible strand 1102 and flexible strand 1104) are discussed below in connection with FIGS. 14A-B.

FIG. 12 shows how a flexible member may be configured as larger chain-type links that are received by surface features of each of the housings. The surface features receive the chain-type links and bind the housing within the chain-type link. FIG. 12 shows housing 1204, housing 1208, and housing 1212 held together by chain-type links such as chain link 1202, chain link 1206, and chain link 1210. Chain link 1202, chain link 1206, and chain link 1210 are received by a surface feature (e.g., surface feature 1002 (FIG. 10)) as indicated by the dotted lines shown on housing 1204, housing 1208, and housing 1212.

In some embodiments, each of the plurality of housings (e.g., housing 1204, housing 1208, and housing 1212) may translate freely along its respective chain link as the chain-type link slides within the surface features of the housing. The translation of the housings may allow the medical implant to expand from a closed state to an opened state. The translation of each housing on its respective chain-type link may be limited as the housing reaches the end of the chain-type link (e.g., point 1214) or makes contact with an adjacent chain-type link linked to a respective chain-type link (e.g., point 1216) of another housing. In some embodiments, coatings (e.g., biocompatible lubricants) may be applied to each chain-type link to facilitate the movement of a housing.

FIG. 13 shows housings that are sewn or otherwise held by pockets of one or more flexible fabric- or polymer-based bands. FIG. 13 shows housing 1308, housing 1310, and housing 1312 held together by flexible band member 1302 and flexible band member 1304. In some embodiments, housing 1308, housing 1310, and housing 1312 may be sewn or encapsulated, partially or fully, in between flexible band member 1302 and flexible band member 1304 as indicated by stitching 1306. Additional embodiments incorporating flexible bands (e.g., flexible band member 1302 and flexible band member 1304) are discussed below in connection with FIGS. 15A-B and 16A-B.

Figure 14A:
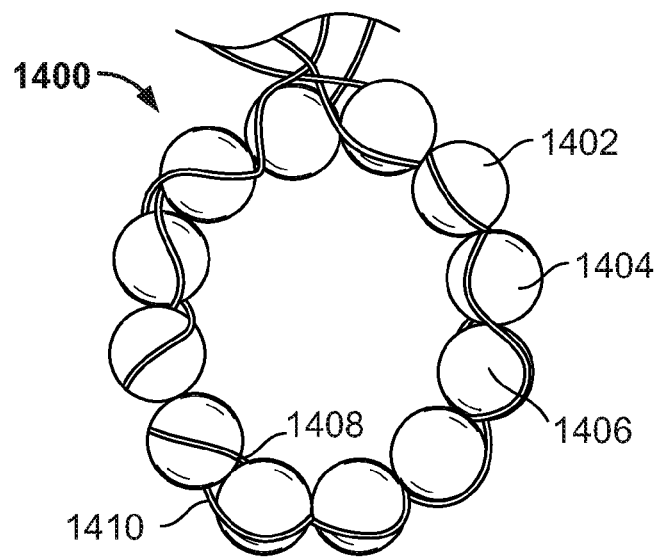
FIG. 14A shows a medical implant, of the type shown in FIG. 11, in a closed state.

FIG. 14A shows how, in a medical implant incorporating a criss-crossing flexible member, each of the housings aligns with each other to form a closed state. In FIG. 14A, medical implant 1400 includes housing 1402, housing 1404, and housing 1406 which are connected through the criss-crossing of flexible strand member 1408 and flexible strand member 1410. In some embodiments, flexible strand member 1408 and flexible strand member 1410 may reside in surface features (e.g., surface feature 1002) located on each of the housings. Medical implant 1400 is currently in a closed state in which the magnetic elements (e.g., magnetic element 106 (FIG. 1)) are magnetically attracted to each other. During this closed state, the tension experienced by the flexible strand member 1408 and flexible strand member 1410 may be reduced.

Medical implant 1400 shows an example of the closed state of a medical implant including flexible strand members in accordance with some embodiments of this disclosure. For example, medical implant 1400 includes a plurality of housings (e.g., housing 1402, housing 1404, and housing 1406) in an annular array. Each housing in the array is oriented so that its respective magnetic element (e.g., magnetic element 106 (FIG. 1)) magnetically attracts the two magnetic elements that are immediately adjacent to it in the array (i.e., the two magnetic elements that are in the housings on the respective opposite sides of the first-mentioned magnetic element in the first-mentioned housing in the array). For example, the magnetic element in housing 1404 is aligned as discussed above and as shown in FIG. 7A-B such that one of its poles (e.g., the north pole) attracts the opposite pole (e.g., the south pole) of the magnetic element in housing 1402. The magnetic element in housing 1404 is also aligned such that its other pole (e.g., the south pole) attracts the opposite pole (e.g., the north pole) of the magnetic element in housing 1406.

Each annularly adjacent pair of housings in the array is connected by flexible strand member 1408 and flexible strand member 1410. Flexible strand member 1408 and flexible strand member 1410 allow the plurality of housings (e.g., housing 1402, housing 1404, and housing 1406) to move away from one another along the length of the flexible strand member 1408 and flexible strand member 1410. However, the amount that the plurality of housings can move away from one another is limited by the flexible strand member 1408 and flexible strand member 1410.

Figure 14B:
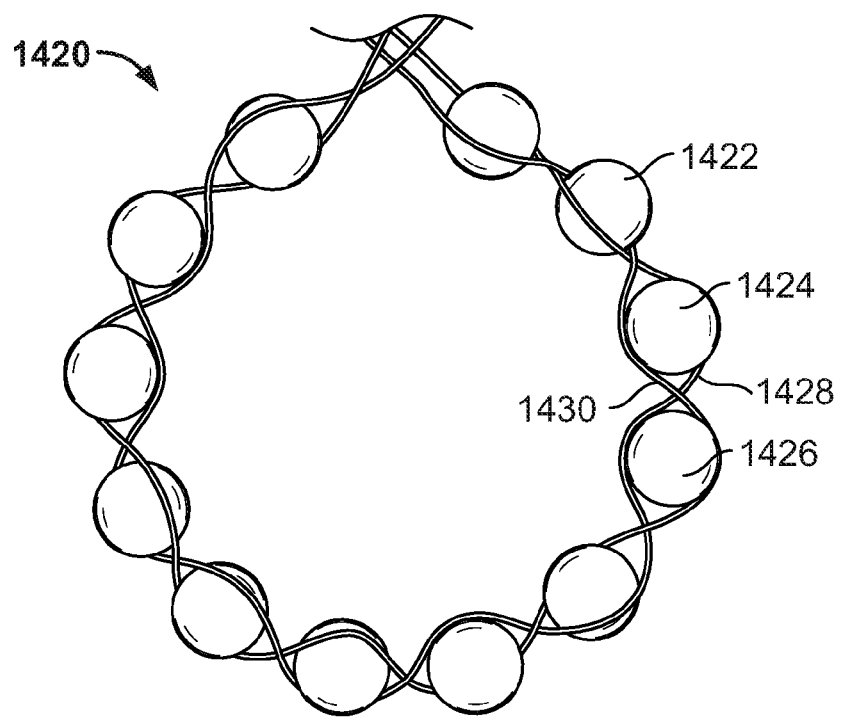
FIG. 14B shows a medical implant, of the type shown in FIG. 11, in an opened state.

For example, in some embodiments, the magnetic attraction, or lack thereof, of the magnetic elements in each of the housings may vary the amount of tension experienced by flexible strand member 1408 and flexible strand member 1410. For example, when magnetically attracting each other, the circumferentially adjacent magnetic elements in each of the plurality of housings may reduce the diameter of the medical implant to a closed state as shown in FIG. 14A. While the medical implant 1400 is in the closed state, the body tissue around which medical implant 1400 is located may be squeezed or have a reduced diameter as medical implant 1400 exerts pressure on the body tissue. During this closed state the tension experienced by flexible strand member 1408 and flexible strand member 1410 may be reduced. In contrast, when the magnetic elements in the circumferentially adjacent housings are not magnetically attracting each other, the body tissue around which medical implant 1400 is located may expand increasing the diameter of medical implant 1400 to an opened state as shown in FIG. 14B. In some embodiments, flexible strand member 1408 and flexible strand member 1410 may elastically expand as the circumference of the medical device is expanded. Tension in flexible strand member 1408 and flexible strand member 1410 may act as a mechanical preventative against further expansion of the body tissue and medical implant 1400.

FIG. 14B shows how, in a criss-crossing flexible member, when sufficient forces exists to separate the housings, the flexible member limits the shape of the medical implant and the distance between the housings in an opened state. In FIG. 14B, medical implant 1420 includes housing 1422, housing 1424, and housing 1426 which are connected through the criss-crossing of flexible member 1428 and flexible member 1430. In some embodiments, flexible member 1428 and flexible member 1430 may reside in surface features (e.g., surface feature 1002) located on each of the housings. Medical implant 1420 is currently in an opened state in which the magnetic elements (e.g., magnetic element 106 (FIG. 1)) are not magnetically attracted to each other (e.g., as a result of a strong external magnetic force). During this opened state, the tension experienced by the flexible member 1428 and flexible member 1430 may be increased.

Flexible member 1428 and flexible member 1430 may function to maintain the arrangement of the plurality of housings (e.g., housing 1422, housing 1424, and housing 1426) in the form of an annular array at all times. While the circumference of the medical implant 1420 may be variable from a smaller size (e.g., as shown in FIG. 14A) when each of the plurality of housings is in contact with its two immediately adjacent neighboring housings (e.g., housing 1422 and housing 1426 in the case of housing 1424), to a larger size when each of the plurality of housings has moved away from its neighboring housings, the annular shape of medical implant 1420 is maintained by flexible member 1428 and flexible member 1430.

Figure 15A:
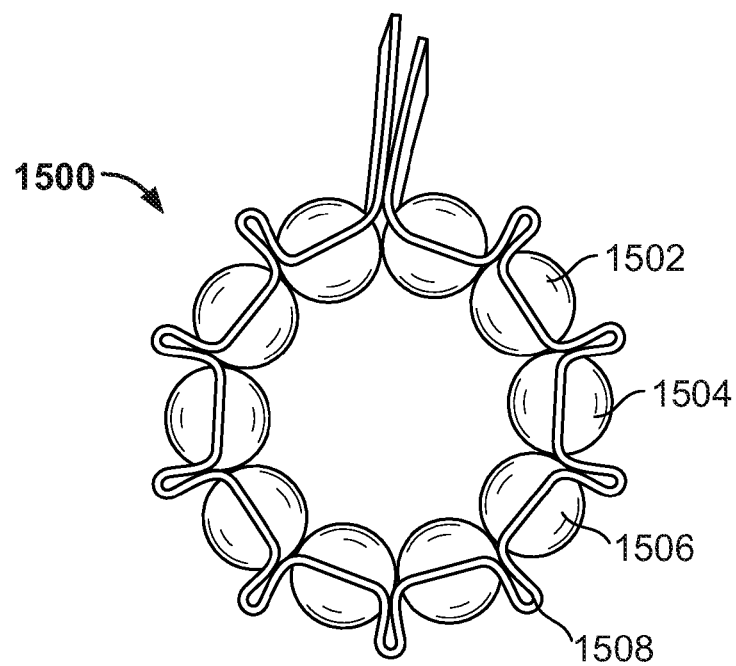
FIG. 15A shows a medical implant, of the type shown in FIG. 13, in a closed state.

FIG. 15A shows how, in a flexible fabric or polymer-based band, each of the housings aligns with each other to form a closed state. In FIG. 15A, medical implant 1500 includes housing 1502, housing 1504, and housing 1506 which are connected through the flexible band member 1508. In some embodiments, flexible band member 1508 may correspond to flexible band member 1302 and/or flexible band member 1304 (FIG. 13). Each housing in the array is oriented so that its respective magnetic element (e.g., magnetic element 106 (FIG. 1)) magnetically attracts the two magnetic elements that are immediately adjacent to it in the array as discussed above. For example, the magnetic element in housing 1504 is aligned with the magnetic element in housing 1502 and the magnetic element in housing 1506.

In some embodiments, flexible band member 1508 may reside in surface features (e.g., surface feature 1002) located on each of the housings. In some embodiments, the housings may be sewn into or encapsulated by flexible band member 1508 as described above in connection with FIG. 13. Medical implant 1500 is currently in a closed state in which the magnetic elements (e.g., magnetic element 106 (FIG. 1)) are magnetically attracted to each other. During this closed state, the tension experienced by the flexible band member 1508 may be reduced.

Each annularly adjacent pair of housings in the array is connected by flexible band member 1508. Flexible band member 1508 allows the plurality of housings (e.g., housing 1502, housing 1504, and housing 1506) to move away from one another along the length of the flexible band member 1508. However, the amount that the plurality of housings can move away from one another is limited by the flexible band member 1508.

For example, in some embodiments, the magnetic attraction, or lack thereof, of the magnetic elements in each of the housings may vary the amount of tension experienced by flexible band member 1508. For example, when magnetically attracting each other, the circumferentially adjacent magnetic elements in each of the plurality of housings may reduce the diameter of the medical implant to a closed state as shown in FIG. 15A. While the medical implant 1500 is in the closed state, the body tissue around which medical implant 1500 is located may be squeezed or have a reduced diameter. During this closed state the tension experienced by flexible band member 1508 may be reduced.

In some embodiments, flexible band member 1508 may shorten its circumferential length via structural features in response to the medical device obtaining a closed state as shown in FIG. 15A. In some embodiments, the area or position of structural features in flexible band member 1508 (e.g., areas predetermined to fold) may be determined by pre-creased or pre-crimped areas of the material that makes up flexible band member 1508. Alternatively, the area or position of structural features may change during each expansion or contraction of the medical implant. In some embodiments, the position of structural features may depend on the size and shape of the housings (e.g., housing 1502, housing 1504, and housing 1506) of medical implant 1500, or the strength of the magnetic elements within each of the housings.

Figure 15B:
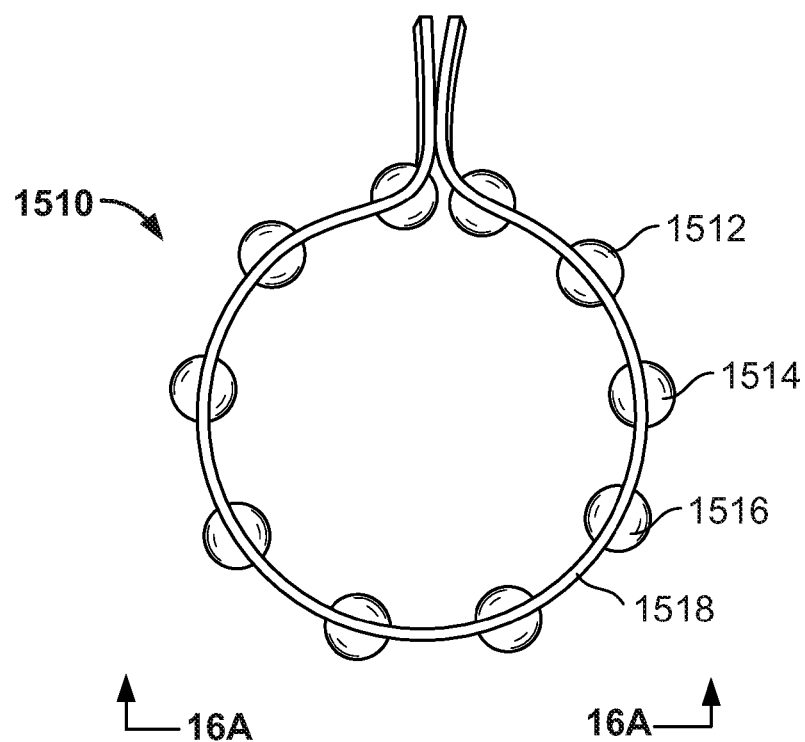
FIG. 15B shows a medical implant, of the type shown in FIG. 13, in an opened state.

FIG. 15B shows how, in a flexible fabric or polymer-based band, when sufficient forces exists to separate the housings, the flexible band limits the shape and distance between the housings to form an opened state. The housings are limited by the flexible band connecting each of the housings. In FIG. 15B, medical implant 1520 includes housing 1512, housing 1514, and housing 1516 which are connected through flexible member 1518. In some embodiments, flexible band member 1518 may reside in surface features (e.g., surface feature 1002) located on each of the housings. Medical implant 1510 is currently in an opened state in which the magnetic elements (e.g., magnetic element 106 (FIG. 1)) are not magnetically attracted to each other (e.g., as a result of a strong external magnetic force). During this opened state, the tension experienced by the flexible band member 1508 may be increased. In addition, any structural features (e.g., folds) of flexible band member 1508 (FIG. 15A), which were present during the closed state of medical implant 1500 (FIG. 15A) may be reduced (e.g., unfolded) while obtaining an opened state as shown in FIG. 15B.

Flexible band member 1518 may function to maintain the arrangement of the plurality of housings (e.g., housing 1512, housing 1514, and housing 1516) in the form of an annular array at all times. The circumference of the medical implant 1510 is variable from a smaller size (e.g., as shown in FIG. 15A) when each of the plurality of housings is in contact with its two immediately adjacent neighboring housings (e.g., housing 1512 and housing 1516 in the case of housing 1514), to a larger size when each of the plurality of housings has moved away from its neighboring housings as permitted by flexible band member 1518. It should be noted any circumferential size between the smaller and larger sizes may also occur and may provide a medical function.

Figure 16A:
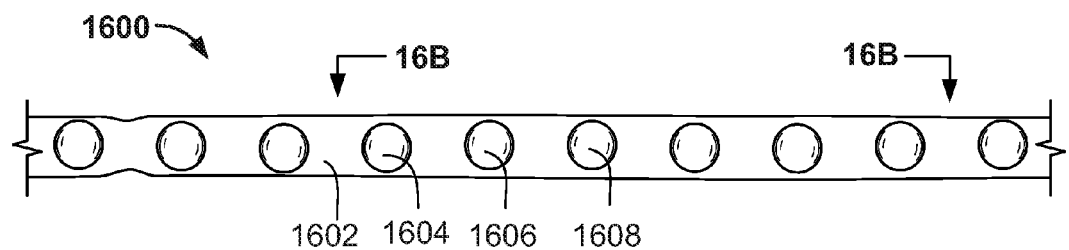
FIG. 16A shows a side view, taken from line 16A-16A of FIG. 15B, of an opened state of a section of a medical implant of the type shown in FIGS. 13, 15A, and 15B.
Figure 16B:
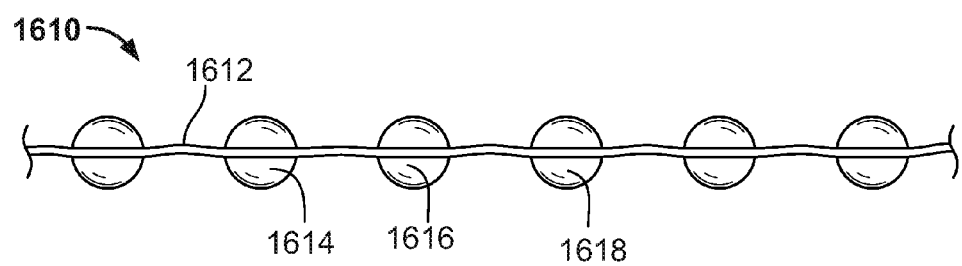
FIG. 16B shows a top view, taken from line 16B-16B of FIG. 16A, of an opened state of a section of a medical implant of the type shown in FIGS. 13, 15A, 15B and 16A.

FIG. 16A shows a side view of an opened state of a medical implant, in which each of the housings is connected by a flexible band. Medical implant 1600 displays flexible band member 1602 connecting housing 1604, housing 1606, and housing 1608. FIG. 16B shows a corresponding top view of an opened state of a medical implant, in which each of the housings is connected by a flexible band. Medical implant 1610 displays flexible band member 1612 connecting housing 1614, housing 1616, and housing 1618. In medical implant 1600 and medical implant 1610, each of the housings is positioned at equal intervals along the length of flexible band member 1602 and flexible band member 1612, respectively. In some embodiments, the positions of housings along a member (e.g., flexible band member 1602 and flexible band member 1612) may vary in order to accommodate specific medical functions or the strength or number of magnetic elements in the medical implant.

For example, in some embodiments, each housing may have a varying number of magnetic elements (e.g., magnetic element 106 (FIG. 1)) in each housing (e.g., as discussed in connection with FIG. 5), or each magnetic element may have a varying amount of strength as discussed above. In some embodiments, the distance between housings along the length of a member in the medical implant may depend on these variations. For example, housings containing strong magnetic elements may be further apart than housings containing weak magnetic elements. Alternatively, magnetic elements may be arranged along the length of the member by their relative strength. For example, in a medical implant featuring strong magnetic elements, adjacent magnetic elements may be spaced further apart. Alternatively, strong magnetic elements may be positioned adjacent to weak magnetic elements, or housings containing multiple magnetic elements may be adjacent to housings with only a single magnetic element. In some embodiments, the specific number or strength of magnetic elements may depend on the particular medical function to be achieved by the medical implant as discussed above.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, or examples relating to one embodiment may be combined with any other embodiment in a suitable manner to achieve suitable results. For example, any description or example relating to a magnetic element may be applied to any description relating to other magnetic elements or to housings containing those magnetic elements. Likewise, any description or example relating surface features on any one of the housings may be applied to all other housings. Any description or example relating to magnetic elements or housings, or surface features on those housings, may also be applied to any description relating to members. Furthermore, any medical implant as shown or described herein may include or incorporate any feature or limitation described throughout this disclosure. It should also be noted that the systems and/or methods described above may be applied to, or used in accordance with other systems and/or methods.

It should also be understood that the foregoing is only illustrative of the principles of the invention, and that various modifications can be made by those skilled in the art without departing from the scope and spirit of the invention. For example, the numbers, sizes, and shapes of various components shown herein are only some illustrations of what can be done, and many variations of these parameters are possible. It will also be appreciated that, while some aspects of what is shown and described herein may be of primary interest in connection for the treatment of gastroesophageal reflux disease and/or with gastric banding, other aspects are of more general interest and applicability. For example, the devices shown and described herein that include both magnetic and elastic components may be used anywhere in a patient's body where such a device can be beneficially applied to a tissue structure or for the treatment of a disease.

What is claimed is:

1. Apparatus for implanting in a patient's body comprising:
   a first magnetic element;
   a first housing encapsulating the first magnetic element, wherein the first housing allows the first magnetic element to float within the first housing;
   a second magnetic element;
   a second housing encapsulating the second magnetic element; and
   a member connecting the first housing to a second housing; wherein:
   the first magnetic element magnetically interacts with the second magnetic element.

2. The apparatus of claim 1, wherein the second housing allows the second magnetic element to float within the second housing.

3. The apparatus of claim 1, further comprising a third magnetic element encapsulated by a third housing, wherein the third magnetic element magnetically interacts with the first magnetic element and the second magnetic element to produce a radially inward force on a body tissue.

4. The apparatus of claim 1, wherein the member is configured to limit a distance between the first magnetic element and the second magnetic element during circumferential expansion.

5. The apparatus of claim 1, wherein the first housing allows the first magnetic element to float freely to align with an external magnetic field.

6. The apparatus of claim 1, wherein the first housing has spherical shape.

7. The apparatus of claim 1, further comprising a groove in the first housing for receiving the member.

8. The apparatus of claim 1, further comprising a through hole in the first housing for receiving the member.

9. The apparatus of claim 1, wherein the member is capable of elastically expanding about a body tissue from a closed state to an opened state.

10. The apparatus of claim 1, wherein the first housing and the second housing are capable of translating on the first member.

11. The apparatus of claim 1, further comprising a plurality of magnetic elements encapsulated in the first housing.

* * * * *